United States Patent
Thorne et al.

[19]

[11] Patent Number: 5,951,525
[45] Date of Patent: Sep. 14, 1999

[54] MANUAL SAFETY MEDICAL NEEDLE APPARATUS AND METHODS

[75] Inventors: David L. Thorne, Kaysville; Gale H. Thorne, Jr., Bountiful, both of Utah

[73] Assignee: Specialized Health Products, Inc., Bountiful, Utah

[21] Appl. No.: 09/021,586

[22] Filed: Feb. 10, 1998

[51] Int. Cl.$^6$ .................................................. A61M 5/32
[52] U.S. Cl. ........................ 604/198; 604/192; 604/162
[58] Field of Search .................................. 604/198, 192, 604/167, 171, 162; 606/222

[56] References Cited

U.S. PATENT DOCUMENTS

| | | | |
|---|---|---|---|
| 3,574,306 | 4/1971 | Alden | 128/214 |
| 4,631,058 | 12/1986 | Raines | 604/263 |
| 4,676,783 | 6/1987 | Jagger | 604/171 |
| 4,966,591 | 10/1990 | Yuen | 604/192 |
| 5,030,212 | 7/1991 | Rose | 604/263 |
| 5,085,639 | 2/1992 | Ryan | 604/110 |
| 5,088,982 | 2/1992 | Ryan | 604/110 |
| 5,108,376 | 4/1992 | Bonaldo | 604/171 |
| 5,112,311 | 5/1992 | Utterberg | 604/177 |
| 5,120,311 | 6/1992 | Safstetter | 604/110 |
| 5,154,699 | 10/1992 | Ryan | 604/116 |
| 5,188,611 | 2/1993 | Orgain | 604/192 |
| 5,219,339 | 6/1993 | Saito | 604/198 |
| 5,266,072 | 11/1993 | Utterberg | 604/177 |
| 5,279,588 | 1/1994 | Nicoletti | 604/250 |
| 5,330,438 | 7/1994 | Gollobin | 604/177 |
| 5,350,368 | 9/1994 | Shields | 604/263 |
| 5,354,281 | 10/1994 | Chen | 604/177 |
| 5,409,461 | 4/1995 | Steinman | 604/110 |
| 5,433,703 | 7/1995 | Utterberg | 604/52 |
| 5,498,241 | 3/1996 | Fabozzi | 604/177 |
| 5,501,672 | 3/1996 | Firth | 604/177 |
| 5,505,711 | 4/1996 | Arakawa | 604/171 |
| 5,549,571 | 8/1996 | Sak | 604/198 |
| 5,562,636 | 10/1996 | Utterberg | 604/263 |
| 5,562,637 | 10/1996 | Utterberg | 604/263 |
| 5,704,924 | 1/1998 | Utterberg | 604/263 |
| 5,746,215 | 5/1998 | Manjarrez | 128/763 |
| 5,772,638 | 6/1998 | Utterberg | 604/263 |
| 5,779,679 | 7/1998 | Shaw | 604/158 |

FOREIGN PATENT DOCUMENTS

| | | |
|---|---|---|
| 0008451 | 8/1979 | European Pat. Off. . |
| 0033207 | 1/1981 | European Pat. Off. . |
| 0253990B1 | 5/1987 | European Pat. Off. . |
| 0436646B1 | 9/1989 | European Pat. Off. . |
| 0558162A2 | 9/1989 | European Pat. Off. . |
| 0558162B1 | 9/1989 | European Pat. Off. . |
| 0494932B1 | 9/1990 | European Pat. Off. . |
| 0443735A1 | 1/1991 | European Pat. Off. . |
| 0475857B1 | 8/1991 | European Pat. Off. . |
| 0534000A2 | 11/1991 | European Pat. Off. . |
| 0534000B1 | 11/1991 | European Pat. Off. . |
| 0499077A1 | 1/1992 | European Pat. Off. . |
| 0521145B1 | 1/1992 | European Pat. Off. . |
| 0566769A1 | 4/1992 | European Pat. Off. . |
| 0566769B1 | 4/1992 | European Pat. Off. . |
| 0615765A1 | 2/1994 | European Pat. Off. . |
| 0664139A1 | 1/1995 | European Pat. Off. . |
| 0745399A1 | 5/1995 | European Pat. Off. . |
| 0692277A2 | 7/1995 | European Pat. Off. . |
| 08206195 | 11/1995 | European Pat. Off. . |
| 0830871A2 | 9/1997 | European Pat. Off. . |

*Primary Examiner*—Michael Buiz
*Assistant Examiner*—Tina T. D. Pham
*Attorney, Agent, or Firm*—Gale H. Thorne; Paul S. Evans

[57] ABSTRACT

A safety medical needle device comprising a mechanism for releasing a latch which holds the needle in place and manually retracting the needle and its sharpened tip into safe containment in one continuous operation. The device may be made from but a single molded part. In the case of a single molded part, the device may consist of a molded body, a medical needle and a protective tube for the needle. The device preferably comprises a pair of winged attachments for use as a medical butterfly apparatus.

10 Claims, 10 Drawing Sheets

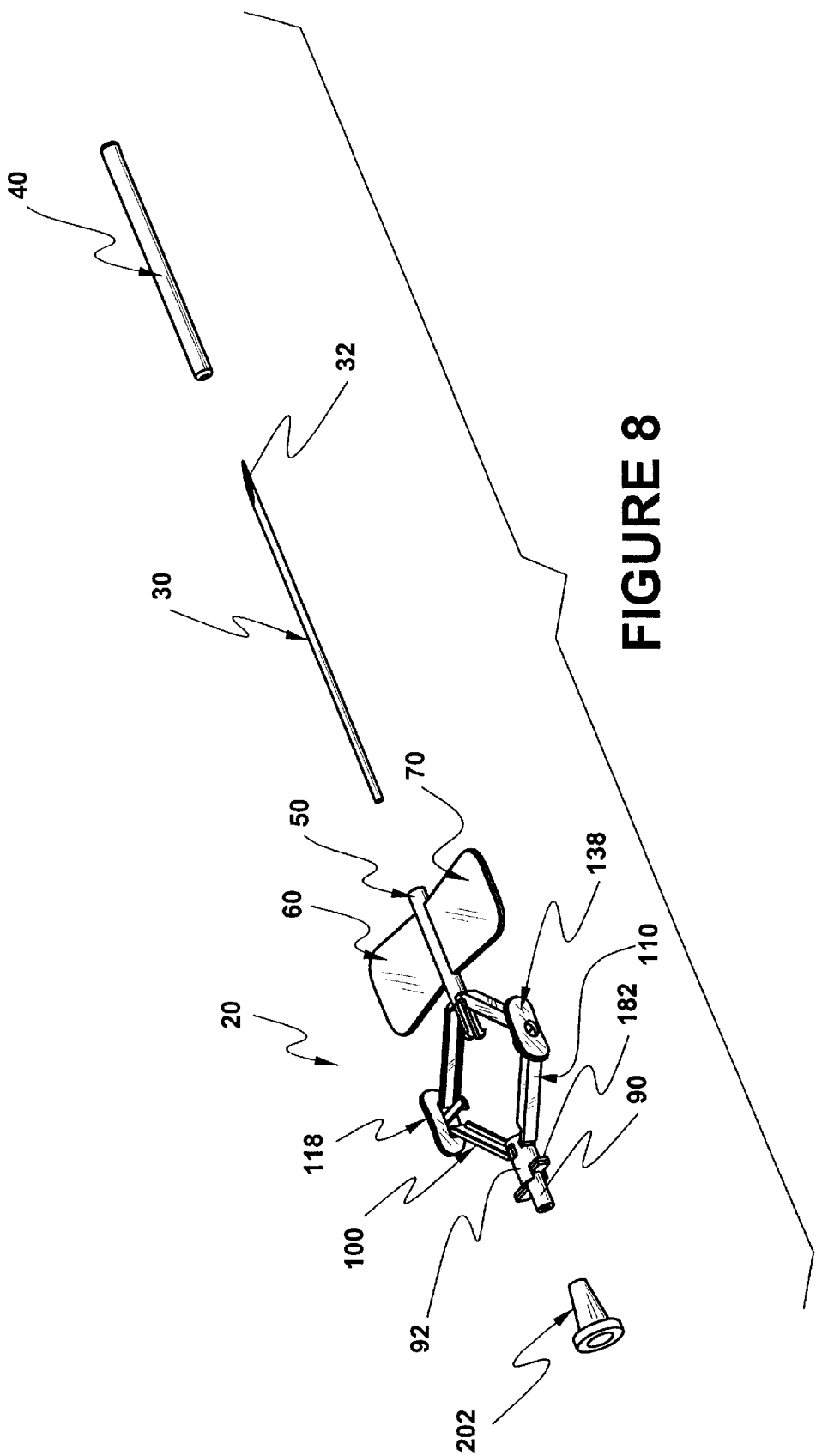

MANUAL SAFETY MEDICAL NEEDLE APPARATUS AND METHODS

BACKGROUND OF THE INVENTION

1. Field of Invention

This invention relates generally to medical needle apparatus and methods and particularly to apparatus comprising medical needles which are retracted from an extended position at which the needle is used to a retracted position where the needle is fully withdrawn and encased within a housing for safe disposal. Further, the invention is related to medical products which may only be used once to eliminate cross contamination from one patient to another. More specifically, the invention is related to safety butterfly devices.

2. Prior Art

Problems associated with inadvertent needle sticks are well known in the art of blood withdrawal, transdermal medication injection, catheter emplacement and other medical procedures involving uses of medical needles, especially winged needle apparatus commonly referenced under the general term of butterflies. Ever increasing attention is being paid to needle stick problems due to the contemporary sensitivity to being exposed to AIDS and Hepatitis.

Commonly, contemporary procedures involving needle withdrawal products require a technician to use one hand to place pressure at the wound site from which a needle is being withdrawn while removing the needle apparatus with the other hand. It is common practice for a tending practitioner to give higher priority to care for the wound than is given to disposal of the needle. Such priority, for common non-safety needle apparatus, either requires an available sharps container within ready reach or another means for safe disposal without leaving the patient's side. In the case of butterfly apparatus, it is common, even for devices which are classed as safety devices, to require two hands to activate an associated safety mechanism. While no sharps container is theoretically required for such a safety mechanism, a sometimes lengthy period of time may elapse from the moment a needle is withdrawn from a patient until the safety mechanism is activated. In such cases, providing adequate care is often compounded by patient condition and mental state (e.g. in pediatrics, ICU's, burn units and psychiatric wards). Under these conditions, it is often difficult, if not impossible, to use appropriate procedures to properly dispose of a contaminated, exposed needle while caring for a patient.

Widespread knowledge and history associated with needle care and disposal problems have resulted in conception and disclosure of a large number of devices each of which represents an attempt to provide not only a solution to the problem of needle sticks, but a device which is commercially viable (i.e. cost and price competitive with currently used non-safety needle devices). A disposable medical needle and catheter placement assembly having safety enclosure means is disclosed in U.S. Pat. No. 5,176,655 issued Jan. 5, 1993 to William McCormick, et al. (McCormick). A device based upon McCormick is currently being sold under the name of ANGEL WING™ SAFETY NEEDLE SYSTEM by Sherwood Medical, St. Louis, Mo. 63103. The ANGEL WING™ device comprises a pair of flexible wing-like sections (for which the term butterfly is generally applied) extending outward from a medically disposed shroud (needle guide) which is aligned with a medical needle. In such devices, it is critical to provide stability for an extended needle as well as secure retention of a retracted needle. The Angel Wing device acquires stability for the extended needle (especially during needle insertion) from a stop provided when the wing-like sections are bent upward from a needle insertion plane and pinched together. Once insertion is complete, release of the wing-like sections disengages needle retention to free the needle of any restriction by the stop. As found in Column 6, beginning at line 11, of McCormick, "Upon completion of the intravenous or other technique, to withdraw the needle from the biological tissue, the wings 24 are held generally against the skin with fingers of one hand while the opposite hand is used to grasp the base member 34, bonded to needle 20 and pull it away from the skin puncture site in a proximal direction." When the needle is so pulled into the shroud, a leaf spring guard, distally disposed relative to the shroud, moves to retard extension of the needle to contain the needle within the shroud. Further, the needle is restrained from inadvertently being pulled proximally from the shroud by a pair of flexible straps disposed between the shroud and hub of the needle. The quoted requirement for two hand operation plus disengagement of the needle when the wing-like sections are not upwardly disposed present an opportunity for improvement in a safety device. The Angel Wing™ device comprises a single molded part, a metal clip and an extruded needle cover in addition to the cannula and other tubing associated with the needle itself.

Another butterfly type safety product presently commercially available is the VACUTAINER® Brand Safety-Lok™ Blood Collection Set distributed by Becton Dickinson VACUTAINER Systems, Becton Dickinson and Company, Franklin Lakes, N.J. 07417-1885. This butterfly Collection Set comprises a safety shield which is distally disposed over a medical needle and sharp tip and securely locked thereat as a safety guard. As is true of the Angel Wing™, two hands are required to engage the safety guard. This Collection Set device comprises two injection molded parts and an extruded needle cover in addition to the cannula and other tubing associated with the needle itself. This product lists U.S. Pat. No. 5,120,320 on its labeling.

Generally, other than acceptance of the type of operation offered by such devices, commercial viability is dependent upon manufacturing cost. Purchase decisions in the area in which these devices are used are very cost dependent. If gains in either improvement in safety or in labor savings are not found to make a device sufficiently competitive with contemporary even less safe items, those devices are usually not found to be commercially viable. Motivation for providing a cost competitive butterfly apparatus coupled with improved safety of use of the apparatus resulted in conception of the instant inventions disclosed herein.

BRIEF SUMMARY AND OBJECTS OF THE INVENTION

In brief summary, the novel invention disclosed herein is the basis for devices which dramatically diminish known major problems resulting from injury-related needle sticks which occur when needle tips are bared as medical needles are withdrawn from a patient at the end of a needle insertion procedure. To meet a primary aim of low cost fabrication, the number of injection molded parts required for a needle safety portion of a device based upon the invention may be as few as one. Of course the device requires additional parts comprising such items as an extruded tube used to protect the needle and its tip before use, the needle, and tubing and tubing connectors associated with a particular medical procedure for which the device is designed. Further, the needle is fully and securely affixed to a protective needle guide and shroud while in use and until a predetermined manual operation releases the needle for retraction into protective cover of the shroud. The operation and subsequent retraction requires but a single continuous activity by one hand of a caregiver.

In a preferred embodiment, a device conforming to the invention comprises a body having a centrally disposed needle shroud beyond which a medical needle and its sharp tip extends distally for use. A pair of laterally, oppositely disposed wings are affixed to the shroud for uses commonly associated with medical butterfly products. The needle extends proximally to a needle hub in which it is securely affixed to provide a communicating contact with appropriate tubing and connectors well known in the art for use in diagnostic procedures, blood collection or IV access. Disposed between and hingeably affixed to the hub and shroud are a pair of elongated foldable members which are oppositely disposed in a substantially collapsed state, proximal to the wings, when the needle is being used. When the foldable members are in the collapsed state, the hub comprises a catch which is releasibly but securely affixed to a latch associated with the shroud to lock the needle and hub to the shroud to prevent the needle from inadvertent retraction relative to the shroud and wings.

In the collapsed state, each foldable member comprises a knee transversely disposed to the common axis of the needle and needle hub. The hub is distortable such that, when distorted, the catch is released from the latch. Hinged connections between the hub and each foldable member are disposed first, to cause the hub to be so distorted when the foldable members are squeezed at the knees, and second, to cause the collapsed members to unfold and elongate to a state where each foldable member is in substantially parallel juxtaposition relative to the other member; whereat, in combination, the members are disposed in locked association about the needle. As a result, the needle tip is retracted into protective cover of the shroud as the members approach each other. When the members are disposed and locked about the needle, the sharp tip of the needle is securely and safely enclosed in the shroud. To ensure a safe enclosure, it is important that material selected for the body be substantially incompressible. In this manner the needle tip is safely contained within the shroud, barring any necessity of a metal clip or the like to further secure the needle or its tip. In a preferred embodiment, the collapsed members cooperatively form a substantially closed sheath about the needle, but in any event, the members form a structure of substantially fixed length which safely keeps the needle tip from further exposure.

An extruded tube is preferably employed to cover the needle prior to use. The tube is removed to prepare the medical needle for a medical procedure.

In a preferred method of use, the extruded tube is removed from covering the needle and needle tip. Then, the device is used in a medical procedure, after which the needle and needle tip are retracted into safe enclosure within the members and shroud by a single hand's activity. The activity is initiated by squeezing the hub and then by collapsing the foldable members about the needle until a secure, locked structure is formed about the needle.

Accordingly, it is a primary object to provide a novel and improved medical needle retracting safety device comprising a body made from a single molded part, a medical needle and a needle cover used to protect the needle and its tip prior to use of the device.

It is a key object to provide an improved medical needle retracting safety device which comprises wings like those used in medical butterfly devices.

It is an important object to provide an improved medical needle retracting safety device which comprises a releasible latch which is normally latched, but which is releasible by a predetermined manual action.

It is another important object to provide an improved medical needle retracting safety device which comprises latch releases and needle retraction mechanisms which are activated by one continuous single handed activity.

It is a paramount object to provide an improved medical needle retracting safety device which comprises a body made by a single mold and which is deformable to retract a needle into a safe state without need for other supporting parts, such as a metal clip.

These and other objects and features of the present invention will be apparent from the detailed description taken with reference to accompanying drawings.

BRIEF DESCRIPTION OF THE DRAWINGS

FIG. 8 is an exploded perspective of parts of the device seen in FIG. 1.

DETAILED DESCRIPTION OF THE ILLUSTRATED EMBODIMENTS

In this description, unless a specific object is otherwise referenced, the term proximal is used to indicate the segment of a device normally closest to a caregiver or technician when it is being used. In like manner, the term distal refers to the other (generally closer to the patient) end. Reference is now made to the embodiments illustrated in FIGS. 1–12 wherein like numerals are used to designate like parts throughout. In some cases, parts having similar form and function to parts earlier cited are enumerated with prime numerals of the earlier cited parts.

Figure 1:
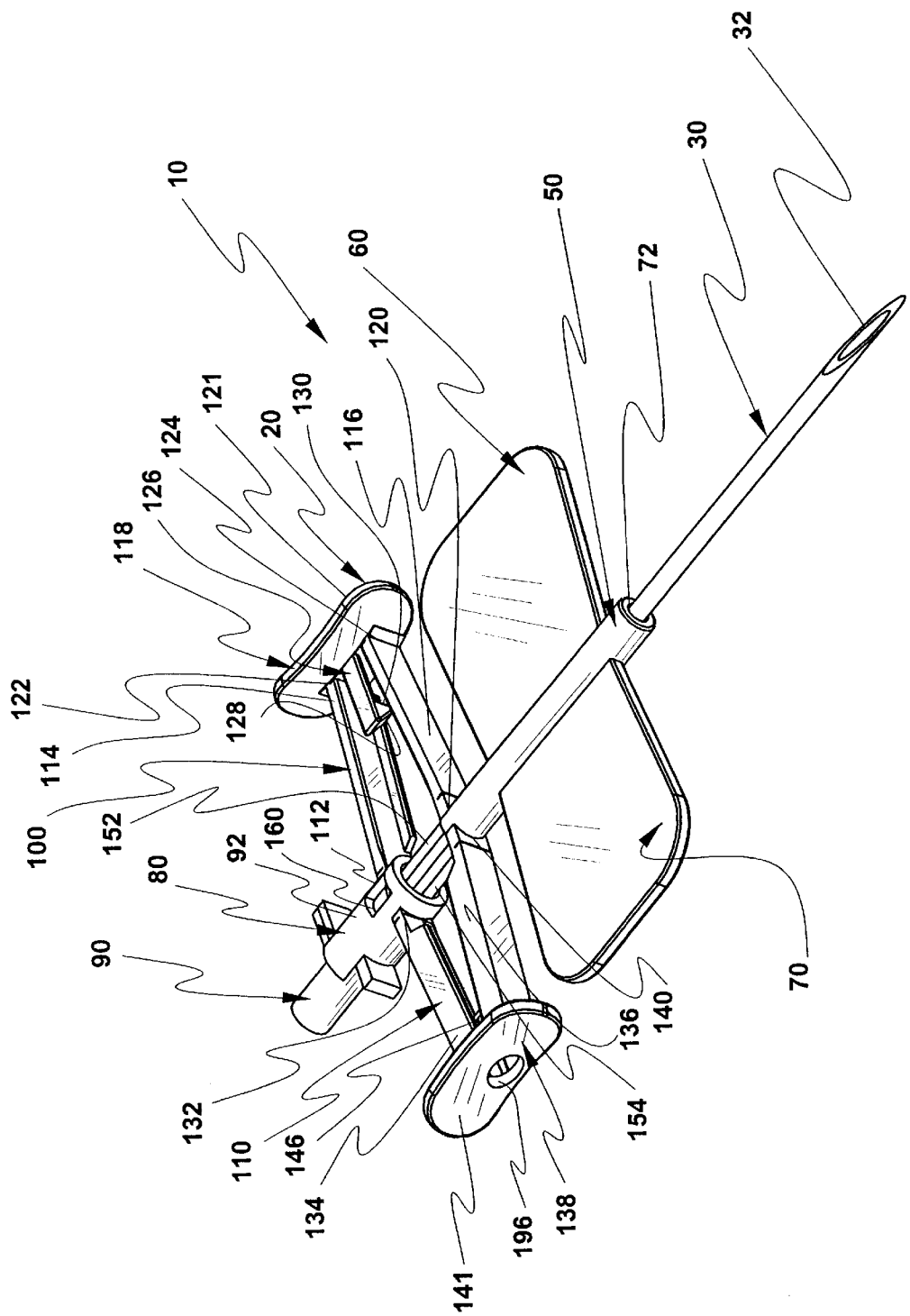
FIG. 1 is a perspective of a safety needle retraction device which conforms with the instant invention, said device being disposed in an as used state with a needle protective cover removed.
Figure 2:
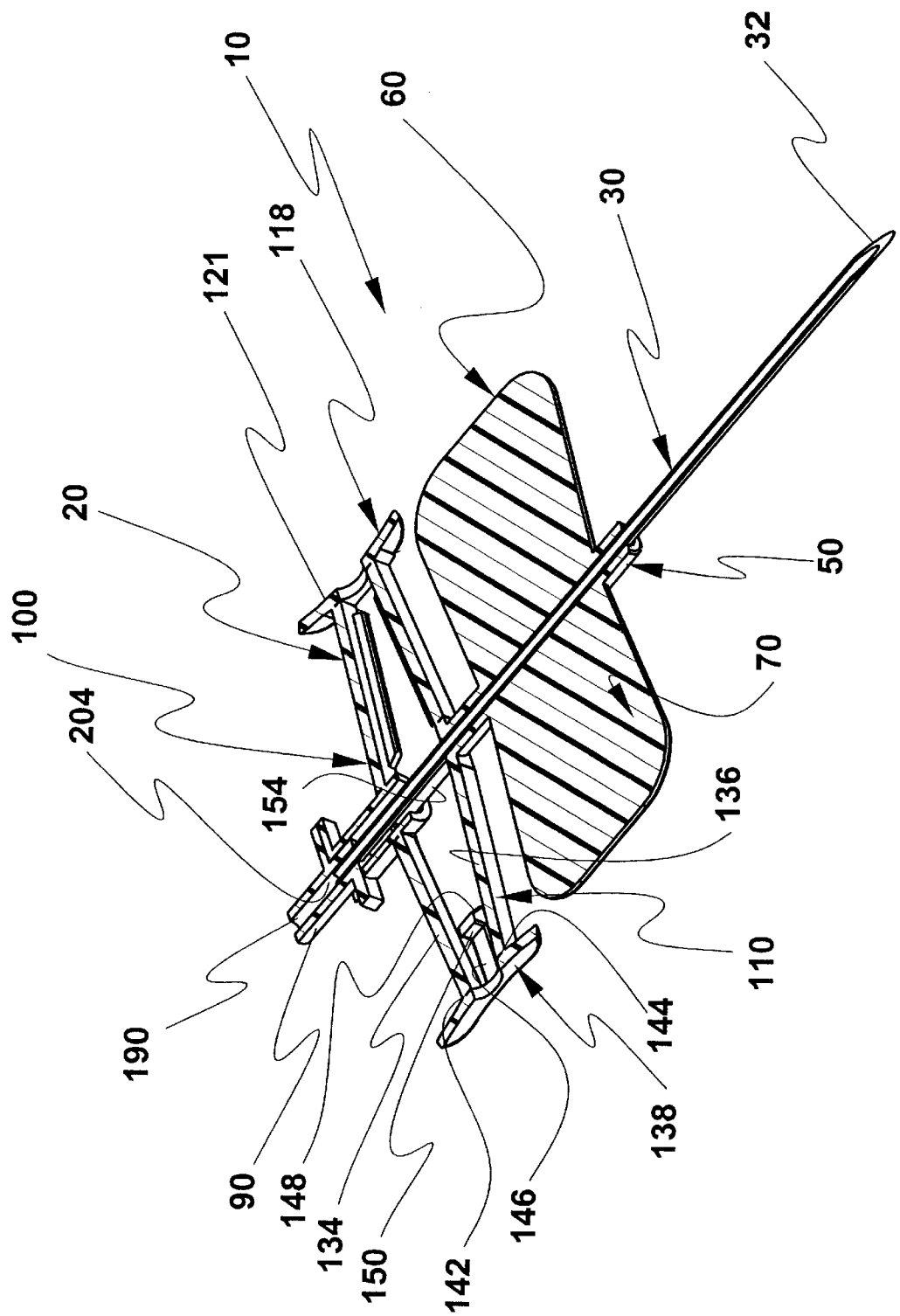
FIG. 2 is a cross section showing an inferior portion of the device seen in FIG. 1.

Reference is now made to FIG. 1 wherein a device 10 which conforms to the instant invention is seen to be prepared for use. Device 10 generally comprises a body 20, a needle 30 (having a sharpened distal tip 32) and a needle protector 40 (not seen in FIG. 1; see FIG. 8). Needle protector 40 is disclosed in more detail hereafter. Body 20 comprises a centrally disposed elongated, hollow cylindrical sheath or shroud 50 having a pair of transversely disposed wings 60 and 70 securely affixed thereto. Shroud 50 comprises a medially disposed lumen 72 which acts as a guide for needle 30.

Proximally, body 20 comprises a needle hub assembly 80. Hub assembly 80 comprises a needle hub 90 and a hub catch member 92. A proximal end of needle 30 (not seen in FIG. 1) is securely affixed in hub 90. Adhesives and methods for securely affixing a needle to a hub are well known in the medical needle arts and devices having such connections are readily commercially available and will therefore not be further addressed herein. The method for forming needle hub and hub catch member 92 is disclosed in detail hereafter.

Proximally hingeably affixed to shroud 50 are a pair of folded legs 100 and 110. Leg 100 comprises a proximal first hinged connection 112 to shroud 50, a proximal section 114 extending laterally from connection 112, a distal section 116 and a knee assembly 118, disposed between sections 114 and 116. Section 116 is also hingeably joined to shroud 50 via a distal second hinged connection 120.

Knee assembly 118 comprises a concave finger plate 121 having a hinged connection 122 to section 114 and a similar hinged connection 124 to section 116. Also extending medially from plate 121 is a locking member 126. Locking member 126 comprises a sloped leading edge 128 transversely disposed to a locking edge 130. Purpose and function of locking member 126 is disclosed in detail hereafter.

In similar fashion, leg 110 comprises a proximal first hinged connection 132 to shroud 50, a proximal section 134 extending laterally from connection 132, a distal section 136 and a knee assembly 138, disposed between sections 134 and 136. Section 136 is also hingeably joined to shroud 50 via a distal second hinged connection 140.

Knee assembly 138 comprises a concave finger plate 141 having a hinged connection 142 (better seen in FIG. 2) to section 134 and a similar hinged connection 144 to section 136. Also extending medially from plate 141 is a locking member 146. Locking member 146 comprises a sloped leading edge 148 transversely disposed to a locking edge 150 (also better seen in FIG. 2). Purpose and function of locking member 146 is disclosed in detail hereafter.

Figure 6:
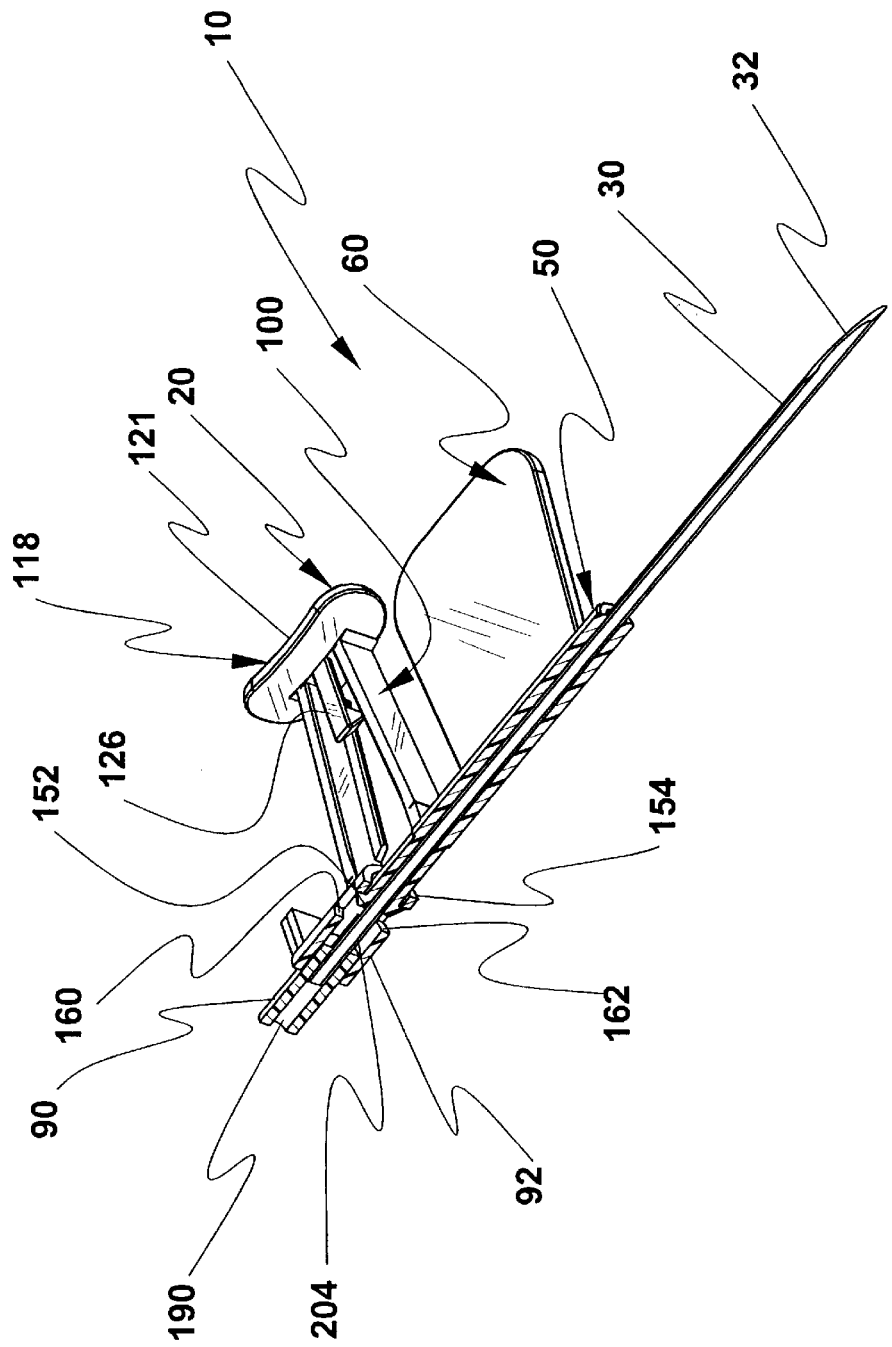
FIG. 6 is a lateral cross section of the device as seen in FIG. 1.

It should be noted that device 10 is disposed in an "as used" state in FIG. 1. In the "as used" state, needle 30 is securely affixed in hub 90 which is firmly attached to hub catch member 92, this attachment is further disclosed hereafter. Hub catch member 92 is releasibly but securely affixed to shroud 50 by a pair of latch members 152 and 154. Each latch member 152 and 154 comprises a latch 156 and 158, respectively. While device 10 is disposed in the "as used" state, latches 156 and 158 are respectively disposed in catch slots 160 and 162, catch slots being located in respective in superior and inferior sites of hub catch member 92 (as best seen in FIG. 6).

Figure 7:
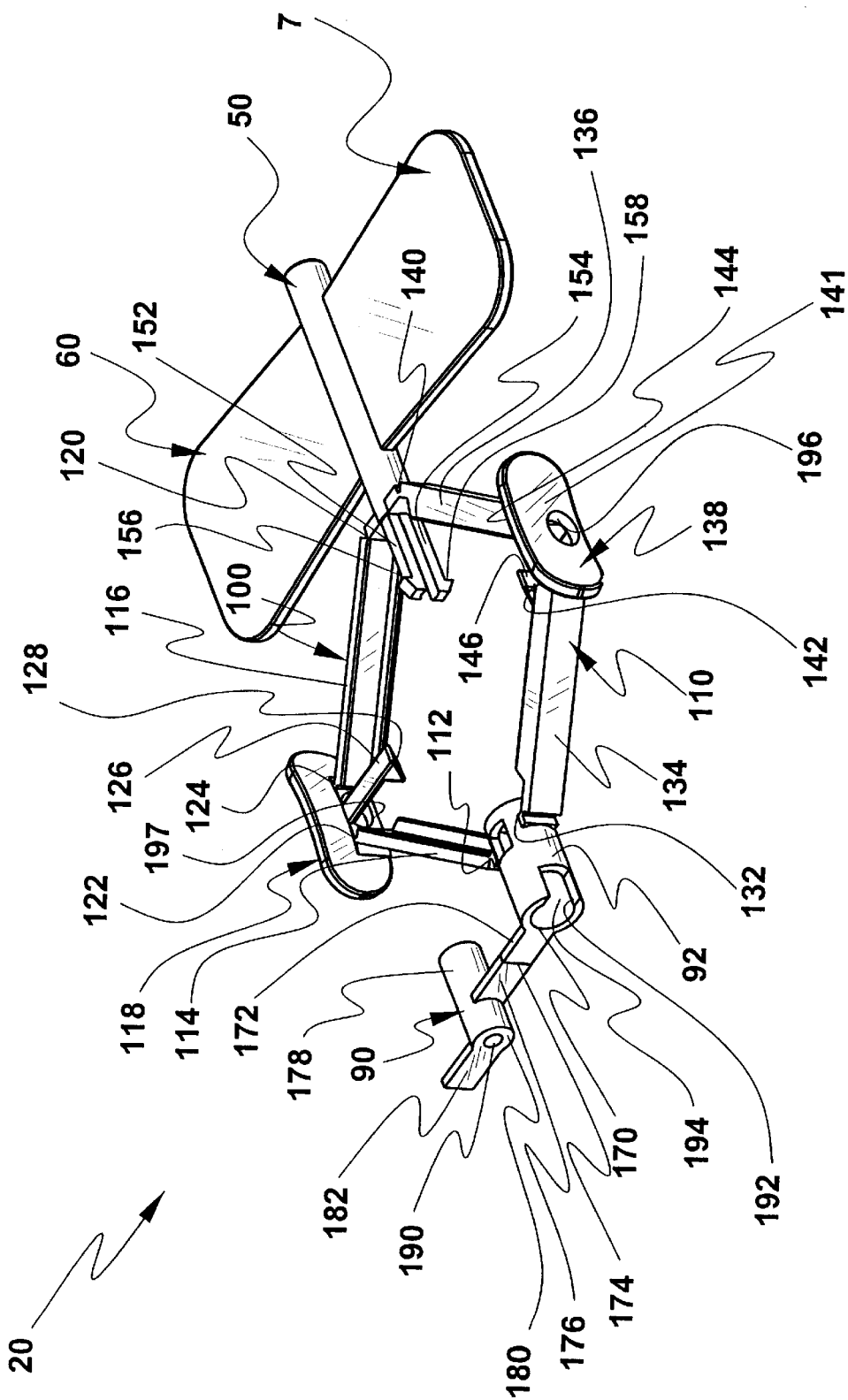
FIG. 7 is an as-molded perspective of a body of the safety needle retractioning device seen in FIG. 1.

Reference is now made to FIG. 7 wherein an "as-molded" state of body 20 is seen. Proximally disposed hub catch member 92 is affixed to leg section 134 through open living hinged connection 132. In a similar manner, member 92 is affixed to leg section 114 through open living hinged connection 112. Extending laterally from a proximal face 170 is a securely affixed tab 172 which communicates through a living hinge 174 with a laterally extending tab 176. Tab 176 is molded to an exterior face 178 of hub 90. Extending laterally from a proximal face 180 of hub 90 is a third tab 182, the purpose of which is disclosed hereafter. Hub 90 also comprises a through hole 190 for receiving and mounting needle 30 and for communicating fluid which traverses needle 30.

Hub member 92 further comprises a locking slot 192 sized to receive and affix tab 182 when hub 90 is rotated 180° to align with hole 190 for needle 30 assembly. Of course, hub member 92 also comprises a lumen 194 sized to receive hub 90. Tab 182 may be securely affixed in slot 192 by adhesion, compression, material displacement or welding, all of such procedures being contemporarily used on materials from which body 20 may be made. Such processes are not, therefore, addressed further herein.

It should be noted that sections 114 and 116 generally have "L" shaped cross sections. Sections 134 and 136 have inverted "L" shaped cross sections. Note also that the eight living hinges (112, 120, 122, 124, 132, 140, 142 and 144) are all molded in an "open" state. That is, when legs 100 and 110 are bent at knee assemblies 118 and 138, to displace body 20 to an as used state, each hinge (112, 120, 122, 124, 132, 140, 142 and 144) is closed to restrict further displacement and thereby form a body which resists further distal travel of needle 30 relative to body 20.

Molding of body 20 is generally accomplished by a single vertical displacement of a mold cavity coupled with three side pulls. A first side pull is axially parallel with needle mounting hole 190, lumen 194 and lumen 72. A second side pull is transverse to the first side pull and is pulled through an access portal 196 disposed in plate 141. The second side pull permits an undercut to be molded into locking member 146 to provide a more secure lock about needle 30 when legs 100 and 110 are compressed together. For similar reasons, the third side pull permits an undercut to be molded into locking member 126 through a portal 197 (see FIG. 7). Such a molding process provides body 20 as a single molded part.

Reference is now made to FIG. 8 wherein parts which make up device 10 plus added parts comprising a needle protecting tube 40 and a luer fitting 202 are seen. As is a standard practice in medical butterfly device manufacture, an inexpensive, elongated plastic tube is commonly used as a needle protector prior to device use. Luer fitting 202 represents attachments to device 10 which may be added so the device can fulfill a particular purpose. Such attachments may include a phlebotomy barrel and rear needle for use in blood acquisition using evacuated blood draw tubes. Other attachments may include a length of medical grade tubing and a luer fitting for syringe use. Still others attachments could be made for needleless connections. All such attachments are well known in the butterfly art and are included within the scope of parts which may be used with device 10. Note that luer fitting 202 may be molded as an integral part of body 20.

Assembly of device 10 with its added parts is straight forward. Fittings, as exemplified by luer fitting 202, are affixed to hub 90. Needle 30 is affixed, presently preferably adhesively, into a channel 204 of hole 190 (See FIGS. 2 and 6). Legs 100 and 110 are contracted to close hinges 112, 120, 122, 124, 132, 140, 142 and 144 and engage latches 152 and 154 into respective slots 160 and 162, as seen in FIGS. 1 and 6. Then protective tube 40 is disposed over needle 30. The so assembled part may then be enclosed in a bubble pack and sterilized for later transport and use. It is preferable that the proximally disposed ends of latch members 152 and 154 be firmly engaged against face 182 of hub 90 to preclude inadvertent proximal movement of needle 30 relative to wings 60 and 70 (not shown). Of course, latch members 152 and 154 should be securely engaged in respective slots 160 and 162 (see FIG. 6) while device 10 is used in a medical procedure.

Figure 3:
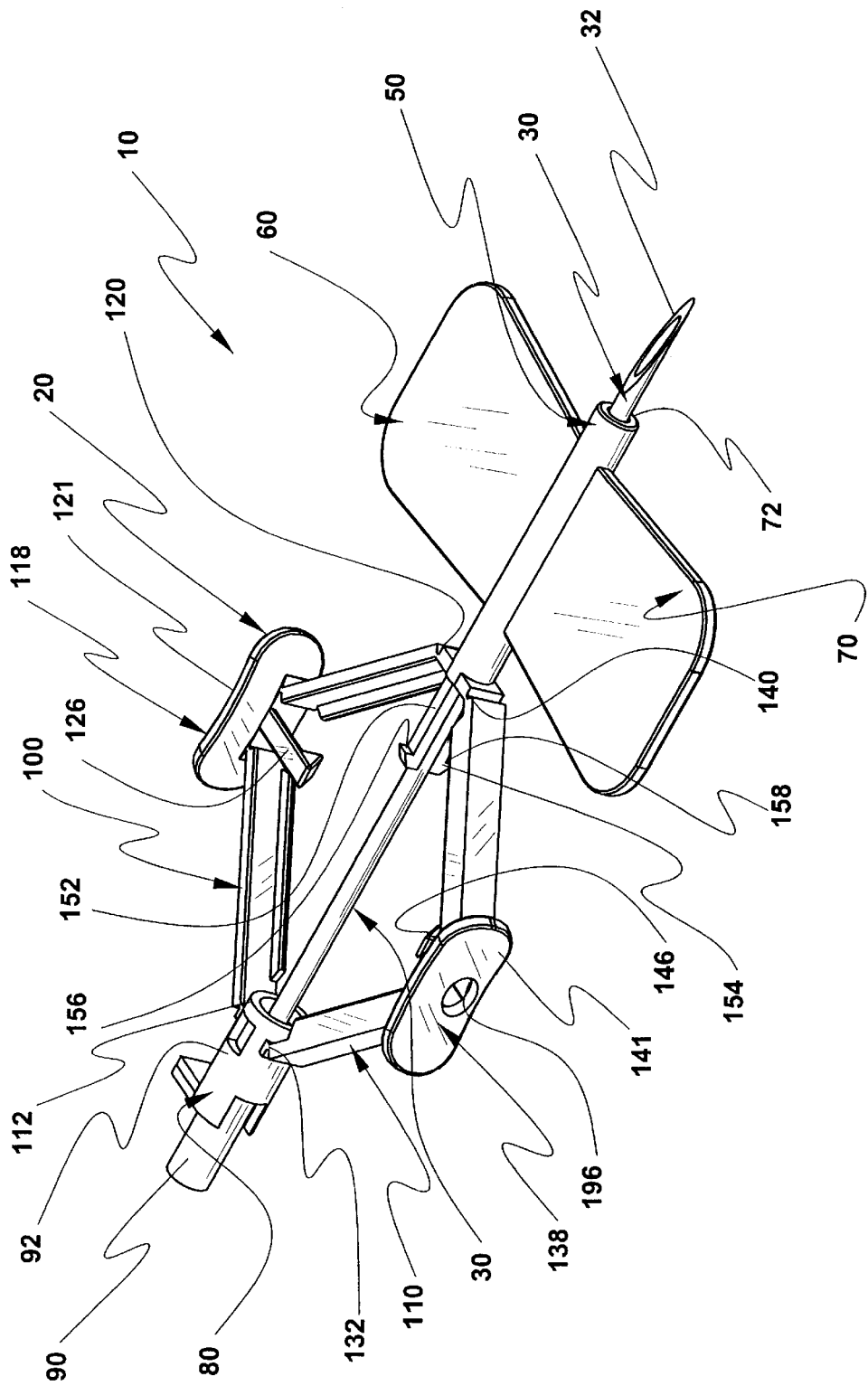
FIG. 3 is a perspective of the device seen in FIG. 1 with the needle partially retracted.
Figure 4:
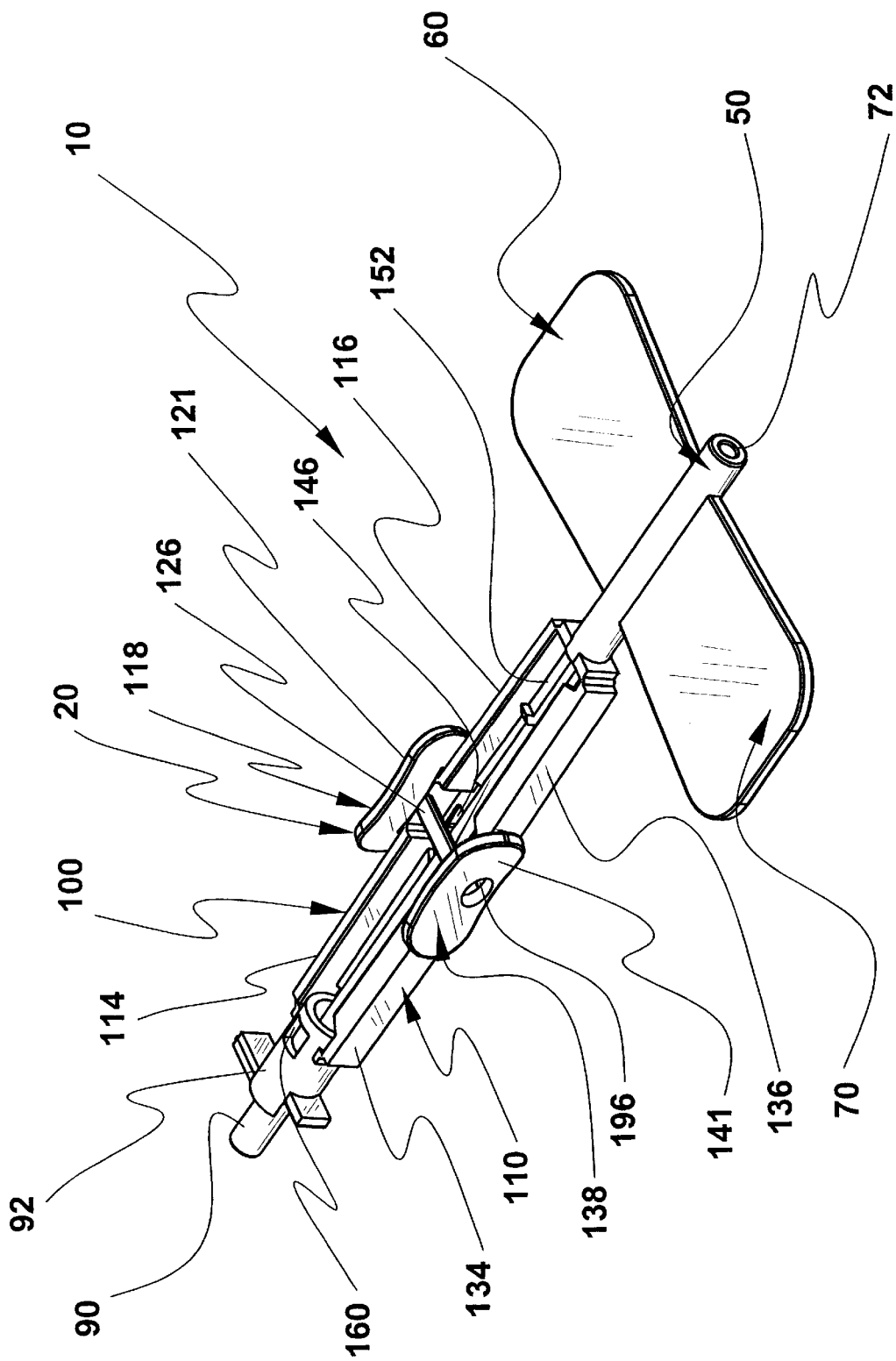
FIG. 4 is a perspective of the device seen in FIG. 1 with the needle fully retracted and locked into a safety housing.
Figure 5:
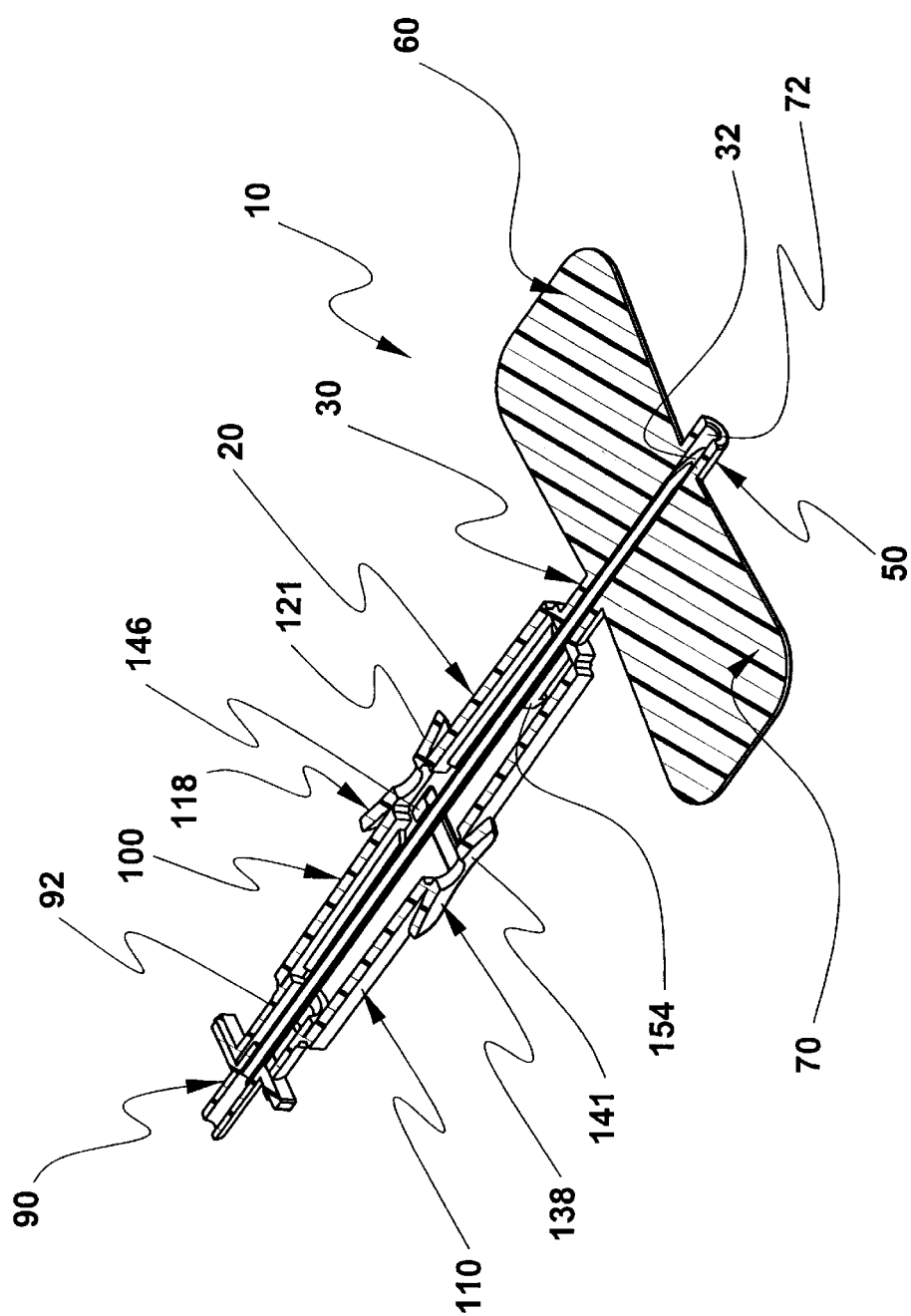
FIG. 5 is a cross section showing an inferior portion of the device as seen in FIG. 4.
Figure 10:
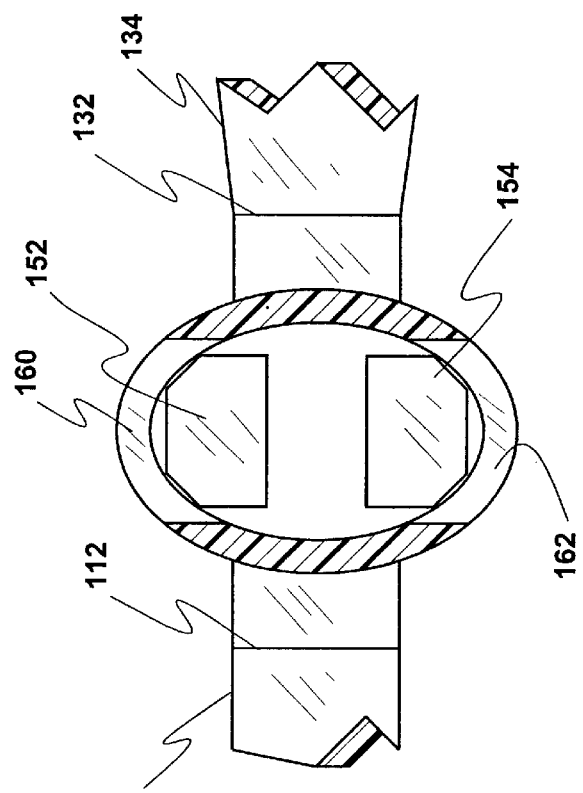
FIG. 10 is a perspective of the portion seen in FIG. 9 wherein a segment is distorted to separate the attachment seen in FIG. 9.
Figure 9:
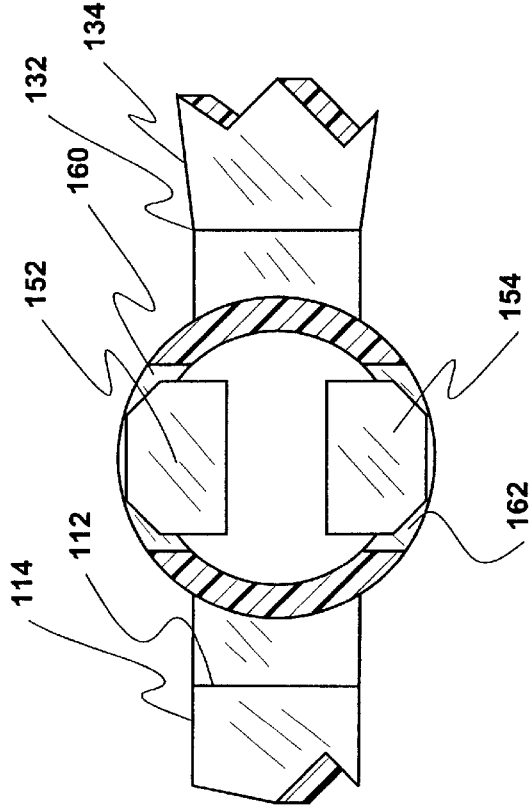
FIG. 9 is a perspective of a portion of a body of the device conforming to the invention showing portions of members which lock about the needle forming a secure attachment.

When the medical procedure is completed, needle 30 is retracted such that needle tip 32 is completely enveloped by shroud 50. Retraction is accomplished by pinching or compressing legs 100 and 110 together. Plates 121 and 141 should be formed as a comfortable digital (e.g. a thumb and forefinger) interface. First pressure on plates 121 and 141 is transferred through leg segments 114 and 134, respectively, to distort hub member 92 from a substantially circular shape as seen in FIG. 9 to a more elliptical shape as seen in FIG. 10. Such distortion frees latch members 152 and 154 from contact with slots 160 and 162 permitting the forces upon plates 121 and 141 to cause legs 100 and 110 to collapse medially toward needle 30. The resulting inward movement of legs 100 and 110 displaces hub 90 (and therefore needle 30 and needle tip 32) proximally relative to shroud 50. A partially retracted needle 30 is seen in FIG. 3.

Continued force against plates 121 and 141 displaces needle tip 32 to be completely sheathed by shroud 50. As legs 100 and 110 are forced together, locking members 126 and 146 securely engage about needle 30 (see FIGS. 4 and 5) to form a substantially rigid and incompressible member which includes the needle and legs 100 and 110. So disposed, needle tip 32 is made inaccessible and the "L" shapes of segments 114 and 116 of leg 100 and inverted "L" shapes of segments 134 and 136 of leg 110 cooperate to form a cover about needle 30.

Figure 12:
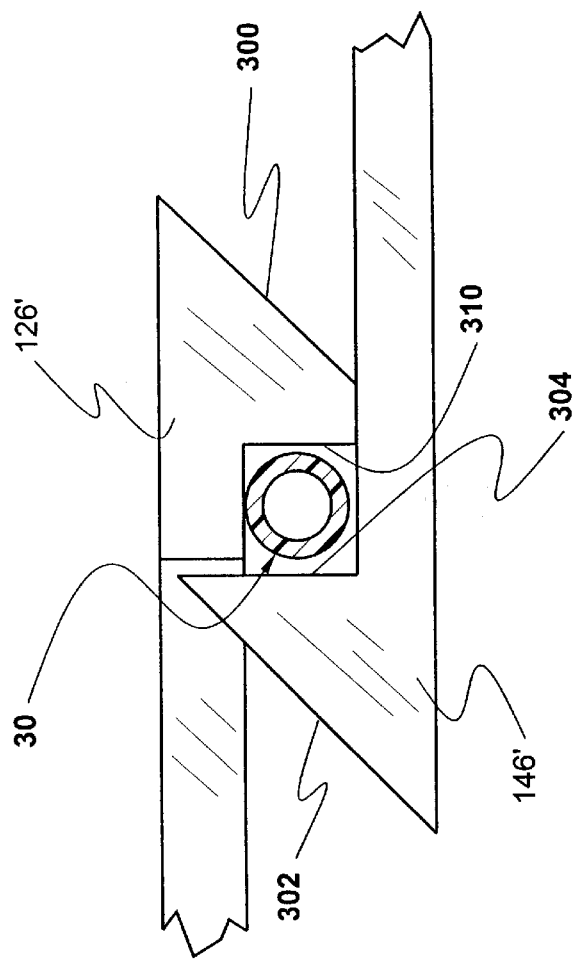
FIG. 12 is a side elevation of the parts seen in FIG. 11.
Figure 11:
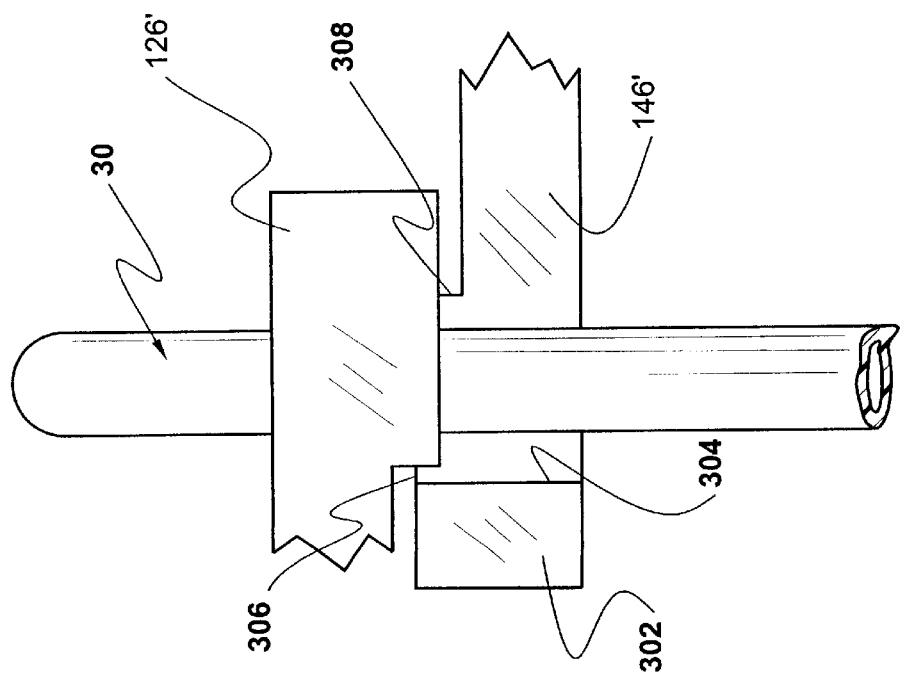
FIG. 11 is a top elevation showing parts which fasten about the needle to assure a secure lock and retention of a retracted needle in a safety enclosure.

It may be desirable to not only lock a locking member (i.e. members 126 and 146) to needle 30, but to lock them to each other or another portion of legs 100 and 110 disposed on an opposite side of needle 30. An example of such an interlock is seen in FIGS. 11 and 12. In this case, none of the locking members are undercut (which may eliminate any need for two of the earlier mentioned side pulls used in molding part 20). Parts similar to locking members 126 and 146 are numbered using primes of earlier referenced similar items for facile reference. Each member 126' and 146' comprises a slanting side 300 and 302, respectively, which causes the member to be displaced away from needle 30 as inward movement compresses leg 100 toward leg 110. Of course, body 20 must be made of material which has sufficient flexibility to be moved away from needle 30 as it is forced into contact therewith, but of sufficient rigidity to return to an original position relative to the needle once past the needle. In FIGS. 11 and 12, member 146' is seen to have a latching face 304. Member 126' comprises a complementary latching shelf 306 disposed to form a redundant locking surface for face 304. In this manner, a lock can be made independent of contact with needle 30. In similar manner, member 146' comprises a locking surface 308 which latches against a complementary face 310 of member 126'.

Body 20 is preferably made from a material which is sufficiently flexible that wings 60 and 70 can be folded together to make needle insertion more facile, but which is sufficiently rigid that legs 100 and 110 form a substantially rigid incompressible structure when locked about needle 30 and members 126, 126', 146 and 146' function as disclosed above. Further, the material must be compatible with living hinge molding requirements. A preferred material is polypropylene, although other materials meeting the above mentioned criteria, such as polyurithane, may be used. The invention disclosed herein may be embodied in other specific forms without departing from the spirit or essential characteristics thereof. The present embodiment is therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed and desired to be secured by Letters Patent is:

1. A safety medical needle apparatus delivered for use with a medical needle in a fully extended state wherefrom the state is changed to a needle retracted safety state by activity resulting from opposing forces, such as forces applied by a single hand, said medical needle apparatus comprising:

a body comprising a distal portion, a medial portion and a proximal portion;

said proximal portion comprising a releasable catch mechanism and a needle hub comprising an axially disposed lumen;

a medical needle comprising a sharp distal tip and a proximal end securely affixed to said needle hub which is axially aligned within said lumen;

said distal portion comprising a shroud, for covering at least the sharp distal tip when the apparatus is in the retracted state, and at least one latch for said releasable catch;

said medial portion comprising a first pair of opposing legs hingeably affixed to a proximal site on said shroud, a second pair of opposing legs hingeably affixed to a distal site on said needle hub in a predisposed relation to said catch;

a pair of opposing actuators, each being hingeably affixed to a leg of the first pair and a leg of the second pair such that compressing one actuator toward the other, by a facile squeeze of a single hand, disengages the catch mechanism from the latch and retracts the hub away from the shroud; and said pair of opposing actuators collectively comprising at least one locking member which securely affixes the apparatus in the retracted state whereby the needle tip is disposed for safety within said shroud.

2. A safety medical needle apparatus according to claim 1 wherein said body comprises but a single molded unitary part.

3. A safety medical needle apparatus according to claim 2 wherein the hub of said body comprises a catch portion hingeably affixed to a needle attachment portion such that a needle lumen in which the needle is affixed is aligned in parallel with an attachment portion receiving lumen during molding to facilitate mold design.

4. A safety medical needle apparatus according to claim 1 wherein said catch mechanism comprises a distortable material which changes when the opposing actuators are compressed to a form which releases the catch from the latch.

5. A safety medical needle apparatus according to claim 1 wherein said distal portion further comprises a pair of butterfly wings.

6. A safety medical needle apparatus according to claim 1 wherein said at least one latch comprises a hook which is firmly engaged with said needle when the needle is retracted to form a substantially rigid body to assure the needle tip is protectively and securely affixed within said shroud.

7. A safety medical needle apparatus according to claim 1 wherein said apparatus further comprises a removable protective tube disposed about said needle to provide protection for the needle and tip prior to use.

8. A method for retracting a medical needle of a safety medical needle apparatus from a needle extended state to a needle retracted safety state, comprising the steps of:

providing the medical needle apparatus comprising a body having a distal portion, a medial portion and a proximal portion;

said proximal portion comprising a releasible catch mechanism and a needle hub comprising an axially disposed lumen;

a medical needle comprising a sharp distal tip and a proximal end securely affixed to said needle hub and axially aligned within said lumen;

said distal portion comprising a shroud, for covering at least the sharp distal tip when the apparatus is in the retracted state, and at least one latch for said releasible latch;

said medial portion comprising a first pair of opposing legs hingeably affixed to a proximal site on said shroud, a second pair of opposing legs hingeably affixed to a distal site on said needle hub in a predisposed relation to said catch;

a pair of opposing actuators, each being hingeably affixed to a leg of the first pair and a leg of the second pair such that compressing one actuator toward the other, by a facile squeeze of a single hand, disengages the catch mechanism from the latch and retracts the hub away from the shroud; and said pair of opposing actuators collectively comprising at least one locking member which securely affixes the apparatus in the retracted state whereby the needle tip is disposed for safety within said shroud;

using the apparatus in a medical procedure;

compressing the actuators toward each other until the catch mechanism disengages from the latch;

continuing to compress the actuators toward each other until the needle tip is retracted into the shroud and the at least one locking member is securely affixed in the fully retracted and locked state whereat the needle tip is disposed within the shroud and the hinged legs combine to form a substantially rigid body to preclude exposing the tip from the shroud thereafter.

9. A method according to claim 8 wherein the compressing step comprises a restricting step of compressing the actuators together with digits of one hand while otherwise attending to a patient with the other hand.

10. A method according to claim 8 wherein the continuing step comprises an additional step of substantially enclosing portions of the needle proximal to the distal tip with conforming parts of opposing legs.

* * * * *